United States Patent
Aderhold et al.

(10) Patent No.: US 10,605,232 B2
(45) Date of Patent: Mar. 31, 2020

(54) METHOD AND DEVICE FOR DETERMINING A POSITION OF DEFECTS OR DAMAGE ON ROTOR BLADES OF A WIND TURBINE IN AN INSTALLED STATE

(71) Applicant: FRAUNHOFER-GESELLSCHAFT ZUR FOERDERUNG DER ANGEWANDTEN FORSCHUNG E.V., Munich (DE)

(72) Inventors: Jochen Aderhold, Wennigsen (DE); Otto Lutz, Bundorf (DE)

(73) Assignee: Fraunhofer-Gesellschaft zur Förderung der angewandten Forschung e.V., München (DE)

( * ) Notice: Subject to any disclaimer, the term of this patent is extended or adjusted under 35 U.S.C. 154(b) by 336 days.

(21) Appl. No.: 15/568,814

(22) PCT Filed: Apr. 20, 2016

(86) PCT No.: PCT/EP2016/058715
§ 371 (c)(1),
(2) Date: Oct. 24, 2017

(87) PCT Pub. No.: WO2016/169959
PCT Pub. Date: Oct. 27, 2016

(65) Prior Publication Data
US 2018/0100489 A1    Apr. 12, 2018

(30) Foreign Application Priority Data

Apr. 24, 2015 (DE) .................. 10 2015 106 366

(51) Int. Cl.
*G01S 19/14*       (2010.01)
*F03D 17/00*       (2016.01)
*G01N 21/88*       (2006.01)

(52) U.S. Cl.
CPC .............. *F03D 17/00* (2016.05); *G01S 19/14* (2013.01); *F05B 2240/2211* (2013.01); *F05B 2260/83* (2013.01); *G01N 2021/8861* (2013.01)

(58) Field of Classification Search
CPC .......... G01S 19/14; G01S 19/34; G01S 19/35; G01S 5/0027; G01S 2205/002
(Continued)

(56) References Cited

U.S. PATENT DOCUMENTS

2007/0297892 A1   12/2007  Kildegaard
2010/0103260 A1    4/2010  Williams
(Continued)

FOREIGN PATENT DOCUMENTS

DE    10 2011 051 205 A1    12/2011
DE    10 2011 017 564 A1    10/2012
(Continued)

*Primary Examiner* — Harry K Liu
(74) *Attorney, Agent, or Firm* — W & C IP

(57) ABSTRACT

The invention relates to a method and a device for determining the position of defects or damage on rotor blades (4) of a wind turbine (1) in an installed state, comprising the steps: a. a localisation instrument (5) is guided along the rotor blade (4) and the defect or damage is detected; b. the localisation instrument (5) has a GPS module (6) by means of which the GPS data of the localisation instrument (5) is detected at the defect or damage; c. the position of the investigated wind turbine (1) is detected by means of the GPS module (6); d. using the position data of the wind turbine (1), the hub height (n) of the wind turbine (1) is retrieved from a database and the distance (d) of the defect or damage of the rotor blade (4) from the hub (34) is calculated in an evaluation unit (8) from the difference
(Continued)

between the GPS data of the localisation instrument (5) and the hub height (n) of the wind turbine and in accordance with the rotor blade position.

14 Claims, 1 Drawing Sheet

(58) Field of Classification Search
USPC .................................................... 342/357.52
See application file for complete search history.

(56) References Cited

U.S. PATENT DOCUMENTS

| | | | |
|---|---|---|---|
| 2010/0209247 A1* | 8/2010 | Becker | F03D 7/0224 416/1 |
| 2011/0013937 A1 | 6/2011 | Ishida | |
| 2012/0300059 A1 | 11/2012 | Stege | |
| 2014/0168420 A1 | 6/2014 | Naderhirn et al. | |
| 2015/0043769 A1* | 2/2015 | Newman | G01N 25/72 382/100 |
| 2015/0377214 A1* | 12/2015 | Du Plessis | F03D 17/00 700/19 |
| 2017/0037832 A1* | 2/2017 | Friedrich | F03D 7/0224 |

FOREIGN PATENT DOCUMENTS

| | | |
|---|---|---|
| DE | 10 2013 103 343 A1 | 10/2014 |
| EP | 1 930 722 A2 | 6/2008 |
| EP | 2 524 649 B1 | 11/2012 |
| WO | 2005/068834 A1 | 7/2005 |
| WO | 2010/051278 A1 | 5/2010 |

\* cited by examiner

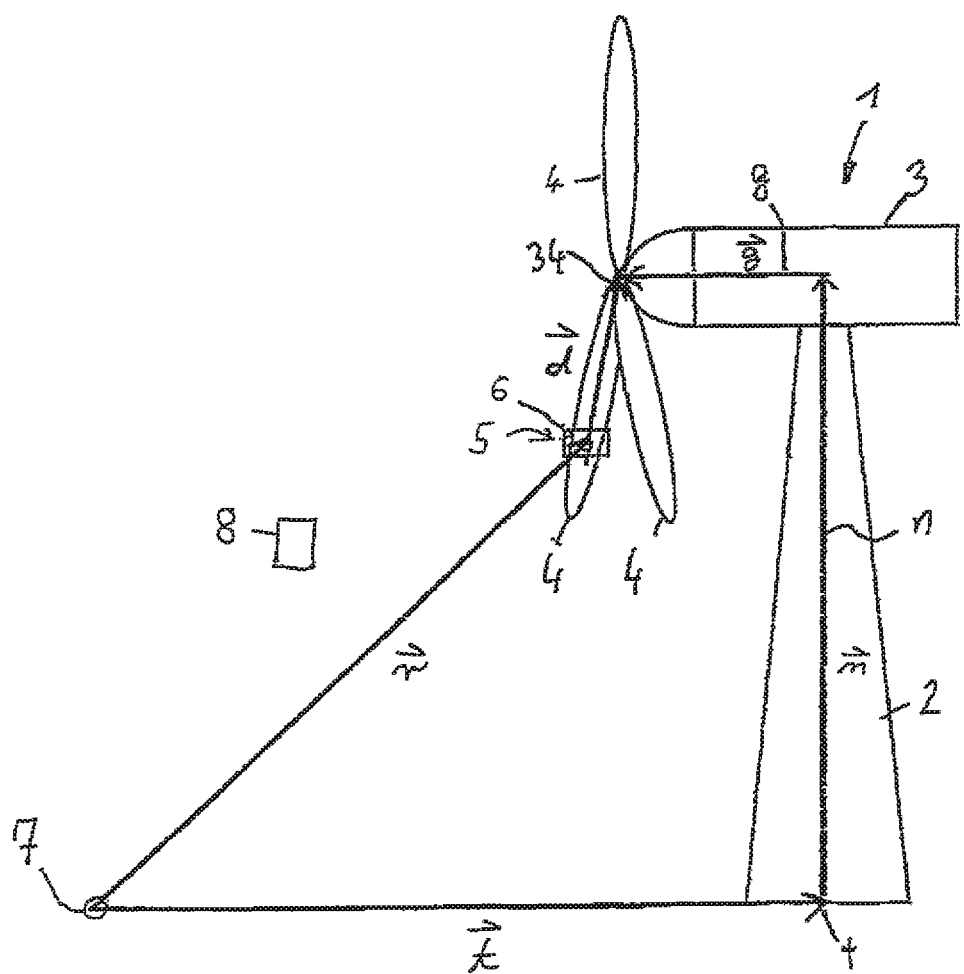

METHOD AND DEVICE FOR DETERMINING A POSITION OF DEFECTS OR DAMAGE ON ROTOR BLADES OF A WIND TURBINE IN AN INSTALLED STATE

The invention relates to a method and a device for determining the position of defects or damage on rotor blades of a wind turbine in an installed state.

Rotor blades of wind turbines are components that are subjected to high loading, and must be examined regularly for structural faults or damage. If faults or damage are found, it may be necessary to effect a repair. Inspection measures and repair measures are preferably performed directly on the wind turbine, which means that the rotor blades are examined and repaired in an installed state on the wind turbine. This saves the very resource-intensive demounting of the rotor blades for examination purposes. For both examination and repair, various access techniques are known, in particular lifters, work platforms, and abseiling of industrial climbers, over the so-called nacelle and the hub, along the rotor blades.

Common inspection techniques are a visual inspection and tapping with a hammer. With all in-situ inspection techniques, it is important to determine and document the position of a found fault, to enable the fault to be found again for a repair. The distance of the defect or damage from the flange of the rotor blade has become established as a usual reference quantity. However, particularly if industrial climbers are used, determining the position of the defect or damage is difficult to accomplish, and is liable to large inaccuracies and a multiplicity of possible errors. An accurate, simple and error-free method, and a device for determining the position of the defects or damage, are therefore desirable.

DE 10 2011 051 205 A1 relates to a system and a method for inspecting wind turbines by means of an inspection system that is moved along the tower of the wind turbines by means of a so-called climbing device. There is an inspection device disposed on the climbing device, the inspection device being configured to examine the rotor blades for indications or damage. The inspection device has position determining instrumentation, which is able to determine the position of the indications or damage. For this purpose, the information relating to the position of the climbing device on the tower is converted into information relating to the corresponding position of the indication or damage along the length of the rotor blade. A measuring device is provided, which calculates the distance from the hub. Moreover, the position determining instrumentation can determine the position of the inspection device by means of a GPS system. Together with other data such as, for example, the height of the tower and the length of the rotor blade, the position of the damage along the course of the rotor blade can be calculated.

EP 1 930 722 A1 relates to a method for non-destructively testing a workpiece, in particular a rotor blade of a wind turbine, for example by means of optical methods or ultrasonic probes. The test method may be executed manually or with use of a tool, the test arrangement comprising a test probe, which is equipped with a transponder for a positioning system. Likewise, a GPS, in particular in differential GPS, can be used. The exact size and shape of the rotor blade is either acquired locally or known by the manufacturer. The position of the measuring probe is effected by means of a triangulation method or the GPS determination.

DE 10 2011 017 564 A1 relates to a method and a system for checking a surface for material defects by means of a flying device that flies along a surface of a rotor blade, and that can capture defects on the surface by means of a camera. The flying device is provided with a position sensor and an inspection means, and GPS sensors can also be used for position measurement.

WO 2010/051278 A1 relates to a method for inspecting rotor blades on wind turbines by means of a flying device, in which the flying device can determine the position relative to the rotor blade by means of GPS signals.

EP 2 527 649 81 relates to a method for inspecting components of a wind turbine that is executed by means of unmanned flying objects, with GPS data being used for remote control.

WO 2005/068834 A1 relates to a method for monitoring the operation of wind turbines, in which GPS receivers are fastened to rotor blades. Via the receivers, the respective position of the rotor blades is determined by means of GPS, to enable operation to be controlled.

The object of the present invention is to provide a method and a device by which it is possible for damage on rotor blades in the installed state to be located in a simple and precise manner, such that the faults or damage can be found again with precision.

According to the invention, this object is achieved by a method having the features of the main claim, and by a device having the features of the coordinate claim. Advantageous embodiments and developments of the invention are disclosed in the dependent claims, the description and in the FIGURE.

The method for determining the position of defects or damage on rotor blades of a wind turbine in the installed provides that a locating instrument is guided along the rotor blade, and the defect or damage is detected, wherein the locating instrument has a GPS module, by means of which the GPS data of the locating instrument are detected at the defect or damage, likewise the position of the examined wind turbine is detected by means of the GPS module and, on the basis of the position data of the wind turbine, the hub height of the wind turbine is retrieved from a database, and the distance of the defect or damage of the rotor blade from the hub is then calculated in an analysis means, in dependence on the rotor blade position, from the difference of the GPS data of the locating instrument and the hub height of the wind turbine. The locating instrument guided along the rotor blade can detect the defect or damage automatically or, alternatively, the locating instrument is guided manually along the rotor blade and activated by a person conducting the examination. It is possible for the position of the examined wind turbine to be deduced on the basis of the GPS data of the locating instrument at the defect. The necessary wind turbine information is stored in a database, for example in a cadaster, from which the required information relating to the wind turbines can be retrieved, if necessary together with their design data, on the basis of the position data. Besides retrieval from a central database, it is possible that the wind turbine data can be stored in the locating instrument or in a separate external database, and the design features, such as the hub height above ground or above mean seal level, can be retrieved on the basis of the wind turbine type. The position of the defect or damage of the rotor blade is then calculated in an analysis means, in dependence on the rotor blade position, from the difference of the GPS data of the locating instrument and the hub height of the wind turbine. The rotor blade position is then either detected automatically by means of the control system of the wind turbine, or can be input, as a parameter to be input, before or during the examination.

A development of the invention provides that the locating instrument is equipped with a camera and/or voice recording means, and the defects or damage are photographed and/or commented, wherein the GPS data of the locating instrument are assigned, preferably assigned automatically, to the respective photo or the voice recording. For this purpose, it is provided that the locating instrument includes a camera, in particular a digital camera, and a module for voice recording, which is preferably wirelessly connected to a microphone, for example a throat microphone that is worn by the person conducting the examination. The person conducting the examination can document found faults by photos, by means of the camera, and by spoken commentary. All photos and voice recordings are identified automatically, or upon command by the person conducting the examination, with the position at the instant of the recording, and are assigned to the respective GPS data, such that there is photographic documentation together with a spoken assessment of the faults of the defects or damage.

In an advantageous development of the invention, the GPS data of the locating instrument are determined by means of a differential measuring system having permanently installed reference stations, as a result of which determination of the position of the locating instrument can be achieved with a high degree of accuracy, without the necessity of installing and setting up a separate, dedicated position sensor, thereby significantly facilitating the practical execution of the measurement. The locating instrument determines the exact location of the wind turbine. For the GPS-based differential measuring system, a plurality of additional position transmitters and at least one receiver are required, whereby it becomes possible, by offsetting the respective signals, for the position of the receiver, which is accommodated, for example, in the locating instrument, to be determined with precision, to a few centimeters, relative to the position transmitter or the position transmitters.

The hub height of the wind turbine may be retrieved from a central database, in which the wind turbine geometry, and in particular the hub height of the wind turbine, are recorded. The retrieval of the data in respect of the hub height of the examined wind turbine on the basis of the GPS data of the locating instrument increases the degree of automation, and consequently the safety against operating errors or incorrect inputs.

A thermographic camera, an ultrasonic sensor, a terahertz spectroscope and/or a tomograph may be disposed on the locating instrument, in order to effect appropriate examination of the rotor blade. The examination may be performed purely optically, on the basis of a thermographic examination, an ultrasonic examination, a terahertz spectroscopy or a tomography, for example a computer tomography. Preferably, only those examination means that enable the locating instrument to be handled and manipulated along the rotor blade surface are used in the locating instrument.

The distance of the defect or damage may be calculated in the locating instrument and stored therein or, alternatively, transmitted to an analysis means, in which the position of the defect or damage relative to the hub, i.e. the distance of the defect from the hub flange, is calculated, for example by vector addition.

A simplification of the calculation is obtained if the rotor blade is examined in a vertical position, i.e., in a position in which the examined rotor blade is oriented parallel to the direction of gravity, or to the normally vertically oriented mast of the wind turbine. If, at the time of measurement, there is an angular position that differs from this, the necessary correction factor can be calculated by means of a trigonometric function.

The angular position of the rotor blade in relation to a defined reference direction, in particular in relation to the vertical, may be transmitted to the analysis means prior to the examination by means of the locating instrument. The angular position may be effected automatically by means of an image analysis if a photograph has been taken of the position of the examined rotor blade.

A development of the invention provides that an automatic defect identification or damage identification is effected, and the distance of the defect or damage from the hub is automatically determined and stored. This may be effected, for example, by a comparison of the rotor blade surface, recorded by means of a camera, thermographic camera, ultrasonic sensor or other examination means, and a predefined image or a standard. If optically visible cracks are detected, this may trigger automatic storage of the associated GPS data in relation to the detected defect; analogously, the position of a thermographic discontinuity or a deviation in the sound transmission behavior is sensed automatically and detected as a defect, and is coupled to the respective GPS information, from which, in turn, the distance of the defect or damage from the hub is then determined and stored.

Advantageously, the locating instrument is guided along the rotor blade at a constant distance from the rotor blade surface, in order to enable reproducible results and comparisons with measurement-value standards or comparison data, or to avoid assignment errors resulting from curvature radii or parallax errors.

The device according to the invention for executing the method described above provides that a locating instrument, which can be moved along an installed rotor blade of a wind turbine, has a GPS module, and is connected to an analysis unit that has access to a database having design data of the examined wind turbine, wherein the distance of a defect or damage from the hub is calculated from the difference of the GPS data of the locating instrument and the hub height of the wind turbine. The analysis unit may be connected to the locating instrument by means of a wireless connection; alternatively, the analysis unit may be integrated in the locating instrument, which may be realized as an instrument that can be guided along in a hands-free manner, wherein, following calculation of the distance of the defect or damage from the hub, this value is stored in the locating instrument or, alternatively, transmitted wirelessly to a decentralized analysis means.

There may be a camera, a thermographic camera, a recording means, an ultrasonic sensor, a terahertz spectroscope and/or a tomograph disposed on the locating instrument, to enable the rotor blade to be checked by optical, thermographic, ultrasound-based, terahertz-based or tomographic examinations. By means of the voice recording means, it is possible for the person conducting the examination to create and add commentary relating to the damage site, so as to ensure better retrievability. The voice commentary enables the quality of the repair to be improved, without the need for the person conducting the examination to be present the repair.

There may be a transmitter and/or a memory for the GPS data disposed on the locating instrument; the calculated distances of the respective defects from the hub may also be stored in the memory.

There may be a receiver and an analysis means disposed in the locating instrument, to enable externally stored data to be received and analyzed as a result of a database retrieval performed on the basis of the available GPS data. In particular, the data of the wind turbine are retrieved, on the basis of the available GPS data, from a cadaster of the wind turbines, the hub height above mean seal level or other reference height is determined, together with the types or wind turbine geometries, and locating of the defect or damage can then be effected with centimeter accuracy on the basis of this data.

The invention is explained in greater detail in the following on the basis of an exemplary embodiment.

The single FIGURE shows a schematic representation of a wind turbine 1, having a tower 2, disposed at the upper end of which there is a so-called nacelle 3. In the nacelle 3 there is normally a generator, by means of which energy of motion is converted into electrical energy. Rotatably mounted on the nacelle 3 there is a rotor having a plurality of rotor blades 4; the rotor blades 4 are attached to a hub 34. In the exemplary embodiment represented, there are three rotor blades 4 attached to the hub 34, the hub 34 being located in the center of the rotor blades 4. When the wind turbine 1 is in operation, the rotor blades 4 may sustain damage. In order not to have to demount the wind turbine 1 for examinations, a locating instrument 5 is guided along the rotor blade 4, when the latter is in the installed state. This may be effected in that the locating instrument 5 is lowered from the hub 34 along the rotor blade 4, for example on a carriage or a sliding device, when the rotor blade to be examined is in a vertical position, i.e. in a position in which the longitudinal extent of the rotor blade 4 is oriented in the direction of gravity. The locating instrument 5 may also be moved from the tip of the rotor blade 4 in the direction of the hub 34. Likewise, it is provided that the locating instrument 5 is guided along the rotor blade surface, for example by an industrial climber; it is equally possible that attached to the respective rotor blade 4 there is a device by means of which the locating instrument 5 is remotely controlled, or is moved automatically over the rotor blade 4 in the longitudinal extent, without direct manipulation, by a mechanic. The locating instrument 5 may be guided along the rotor blade 4 from a work platform.

Disposed on the locating instrument 5 there is a GPS module 6, by means of which the respective position data or GPS data of the locating instrument 5 are captured permanently or upon triggering or upon demand. The position data of the locating instrument 5 that are applied at a defect or damage of the rotor blade 4 are captured by the locating instrument 5 and assigned, either automatically or by an operator, to the respective defect, and either analyzed by the locating instrument 5 itself or, alternatively, transmitted to an analysis means 8. The defect or damage as such may likewise be detected automatically, for example by means of automatic image analysis. The analysis means 8 may be located in direct proximity to the locating instrument 5, for example on a work platform, in the region of the nacelle 3 or of the tower, or on the ground, close to the wind turbine 1. The GPS data are then transmitted, either via a data line or wirelessly, for example via a radio signal, to the analysis means 8. In a variant of the invention, the analysis means 8 is positioned in a control center, such that the respective location data and, if necessary, also images of damage, can be analyzed centrally. The data transmission is then effected by radio communication or by another manner of wireless data transmission.

The locating instrument 5 may be equipped with damage detection means, for example with a camera, a thermographic camera, a voice recording means, an ultrasonic sensor, a terahertz spectroscope or a tomograph, or other detection means. If the locating instrument is used by a person in conjunction with the possibly recorded images, the voice recording means can be used to add an assessment by the person conducting the examination, such that both the damage and the position of the defect or damage can be described in greater detail.

For the purpose of determining the position of the respective damage on the examined rotor blade, the wind turbine 1 is first identified, on the basis of the GPS data of the locating instrument 5, by a database retrieval from a wind turbine cadaster. Starting from a coordinate origin 7, which is the base or reference station for the method and the device for determining the position of the defects or damage on a rotor blade 4, the position of the tower center point t is first assigned to the examined wind turbine 1 from a database, for example the wind turbine cadaster, and the position vector t is calculated. The hub height n is likewise known from technical data sheets and the database, as is the distance g from the tower center point to the hub 34, such that a vector line is known from the vector between the coordinate origin or the reference station 7 and the tower center point t, the hub height n and the distance from the tower center point t, at the level of the hub 34, to the hub 34.

From the position data of the GPS module 6 it is possible to calculate the damage vector $\vec{v}$ between the coordinate origin 7 and the locating instrument 5, such that the distance d can be calculated, as a distance vector $\vec{d}$, from the addition of the position vector $\vec{t}$ between the coordinate origin or the reference station 7 and the tower center point t, the hub height vector $\vec{n}$ and the hub distance vector $\vec{g}$ and the subtraction with the damage vector $\vec{v}$ of the GPS module 6. The formula for this is:

$$\vec{d} = \vec{t} + \vec{n} + \vec{g} - \vec{v}.$$

The position of the defect or damage, as a distance d from the hub 34 to the damage site, enables the defect or damage on the rotor blade 4 to be easily found, or found again, if this has to be removed for servicing or repair. If appropriate, if the damage or defect is not so severe that it has to be rectified immediately, the removal and repair may be effected only as part of a regular servicing. It is made easier for the damage or defect to be found again and, in subsequent examinations, comparisons can be made with the possibly existing damage progress, and a damage logbook can be compiled. If the position of the rotor blade 4 is other than the vertical, a correction function must be calculated by means of the trigonometric function. When the rotor blade 4 is in the horizontal position, determination of the position of the defect or damage on the rotor blade 4 is not possible; the more the longitudinal extent of the rotor blade axis approaches the horizontal, the less is the resolution, or the more imprecise is the determination of the position.

The invention claimed is:

1. A method for determining a position of defects or damage on rotor blades of a wind turbine in an installed state, comprising the steps of:
examining a wind turbine by guiding a locating instrument along a rotor blade and detecting a defect or damage of the rotor blade;
determining a position of the examined wind turbine from GPS data of the locating instrument using a GPS module attached to or which is part of the locating instrument;

determining a position of the defect or damage using the GPS module;

retrieving from a database, on the basis of the determined position of the wind turbine, a hub height of a hub of the wind turbine; and calculating, using an analysis means, a distance of the defect or damage of the rotor blade from the hub in dependence on the rotor blade position, from the difference of the GPS data of the locating instrument and the hub height of the wind turbine.

2. The method as claimed in claim 1, further comprising recording an image and/or voice with a camera and/or voice recorder connected to the locating instrument wherein the defects or damage are photographed and/or voice-recorded, and the UPS data of the locating instrument are assigned to the image and/or the voice recording.

3. The method as claimed in claim 1, wherein the step of determining a position of the examined wind turbine includes obtaining the GPS data of the locating instrument using a differential measuring system having permanently installed reference stations.

4. The method as claimed in claim 1 wherein the hub height of the wind turbine is retrieved from a central database.

5. The method as claimed in claim 1 wherein a thermographic camera, an ultrasonic sensor, a terahertz spectroscope and/or a tomograph is disposed on the locating instrument, and information from the thermographic camera, the ultrasonic sensor, the terahertz spectroscope and/or the tomograph are provided to a remote computer.

6. The method as claimed in claim 1 wherein the distance of the defect or damage is calculated in the locating instrument and stored therein or is transmitted to the analysis means.

7. The method as claimed in claim 1 wherein the rotor blade is examined in a vertical position.

8. The method as claimed in claim 1 further comprising transmitting an angular position of the rotor blade in relation to a defined reference direction to the analysis means prior to the examination by means of the locating instrument.

9. The method as claimed in claim 1 wherein automatic defect identification or damage identification is effected, and the distance of the defect or damage from the hub is automatically determined and stored.

10. The method as claimed in claim 1 wherein during the examining step the locating instrument is guided along the rotor blade at a constant distance from a rotor blade surface.

11. A device for determining a position of defects or damage on rotor blades, comprising:

a locating instrument configured to be moved along an installed rotor blade of a wind turbine; (1), has a GPS module connected to or being tart of the locating instrument; and analysis unit connected to the GPS module, wherein the analysis unit has access to a database having design data of the wind turbine, wherein a distance of a defect and/or damage of the rotor blade from a hub is calculated from a difference of GPS data of the locating instrument and a hub height of the wind turbine.

12. The device as claimed in claim 11, further comprising one or more of a camera, a thermographic camera, a voice recording means, an ultrasonic sensor, a terahertz spectroscope, and a tomograph disposed on the locating instrument.

13. The device as claimed in claim 11 further comprising one or more of a transmitter and a memory for the GPS data disposed on the locating instrument.

14. The device as claimed in claim 11 further comprising a receiver and an analysis means disposed on the locating instrument.

* * * * *